United States Patent [19]

Yabut

[11] 4,146,648
[45] Mar. 27, 1979

[54] CHEMOTHERAPEUTIC COMPOSITION

[75] Inventor: Cynthia A. Yabut, San Diego, Calif.

[73] Assignee: Bristol-Myers Company, New York, N.Y.

[21] Appl. No.: 815,708

[22] Filed: Jul. 14, 1977

[51] Int. Cl.$^2$ .............................................. A61K 31/03
[52] U.S. Cl. ................................................... 424/354
[58] Field of Search ......................................... 424/354

[56] References Cited

U.S. PATENT DOCUMENTS

| 2,238,973 | 4/1941 | Climenko | 424/228 |
| 2,951,014 | 8/1960 | Garman | 424/228 |
| 3,097,135 | 7/1963 | Lynch | 424/228 |

OTHER PUBLICATIONS

Nissen-Meyer et al., Cushing's Syndrome, Diagnosis and Treatment, pp. 141-147 (1972), Wm. Heinemann Med. Books Ltd.

*Primary Examiner*—Jerome D. Goldberg
*Attorney, Agent, or Firm*—Natalie Jensen

[57] ABSTRACT

A therapeutic composition for treating adrenal cortical carcinoma comprising 1,1-dichloro-2-(o-chlorophenyl)-2-(p-chlorophenyl)ethane and an oil carrier or vehicle.

12 Claims, No Drawings

CHEMOTHERAPEUTIC COMPOSITION

The present invention relates to a chemotherapeutic composition for treating a steroid-sensitive cancer. More particularly, the present invention relates to a therapeutic composition for treating adrenal cortical carcinoma in humans comprising 1,1-dichloro-2-(o-chlorophenyl)-2-(p-chlorophenyl) ethane and an oil carrier or vehicle.

Carcinoma of the adrenal cortex is a disease that occurs in all age groups. Tumors appear to originate equally in the left and right adrenals and metastases appear primarily in adjacent structures, especially the kidneys. A functioning adrenal carcinoma commonly produces 17-ketosteroids, sometimes in extremely large quantities. A second group of steroids commonly produced are 17-hydroxycorticosteroids. Production of 17-hydroxycorticosteroids may also be very high, although seldom as high as 17-ketosteroid production.

Preferred treatment of the disease is surgical removal of the tumor; frequently, however, the carcinoma is too far advanced for surgery and/or the condition of the patient is such that adrenalectomy is too risky. In such cases, chemotherapy is used and 1,1-dichloro-2-(o-chlorophenyl)-2-(p-chlorophenyl)ethane is the drug of choice. 1,1-Dichloro-2-(o-chlorophenyl)-2-(p-chlorophenyl)ethane, better known as mitotane, has been found to be effective not only in the reduction of tumor mass, but the reduction of abnormal steroid production as well. (Lubitz, et al., *Journal of the American Medical Association*, Vol. 223, pp. 1,109–1,112, 1973.)

Present evidence indicates that mitotane is only 35–40% absorbed from the gastrointestinal tract when administered as 0.5 g. capsules of dry powder and only 20% absorbed when administered as 0.5 g. tablets of compressed powder (Moy, *Journal of Laboratory and Clinical Medicine*, Vol. 58, No. 2, pp. 296–304, 1961, and Nissen-Meyer and Vogt, *Cushing's Syndrome, Diagnosis and Treatment*, pp. 141–147, William Heinemann Medical Books, Ltd., 1972).

Due to poor absorption of the drug in dry dosage formulations, it has been necessary to administer massive oral doses (i.e., 6 to 20 g. per day) in order to obtain a disease response. These dose levels have often produced toxic side effects.

For the most part, toxicity to the drug has been classified as gastrointestinal toxicity (80% of patients), neuromuscular toxicity (40% of patients), and skin toxicity (14% of patients).

Gastrointestinal disturbances include anorexia, nausea or vomiting, and, in some cases, diarrhea.

Central nervous system depression, manifested by lethargy and somnolescence, is the most commonly observed neuromuscular disturbance. Dizziness or vertigo, muscle tremors, headaches, confusion and weakness have also been noted.

The appearance of cutaneous eruptions due to skin toxicity does not appear to be dose related since, in some instances, the condition has disappeared during treatment even though there was no change in drug dosage.

Other less frequent side effects that have been observed with the drug have involved the eye (visual blurring, diplopia, lens opacity, toxic retinopathy); the genito-urinary system (hematuria, hemmorrhagic cystitis, and albuminuria; and the cardiovascular system (hypertension, orthostatic hypotension, and flushing). Miscellaneous complaints, including generalized aching, hyperpyrexia, and lowered serum protein-bound iodine, have also been noted.

The aforementioned adverse side effects are documented in a clinical study described by Hutter, et al., in the *American Journal of Medicine*, Vol. 41, pp. 581–592 (1966). Mitotane used in this study was made available through the National Cancer Institute as a dry dosage formulation, i.e., 0.5 g. scored tablets.

The effectiveness of mitotane as a chemotherapeutic agent has been seriously hampered by the high incidence of gastrointestinal and CNS side effects, which effects have often necessitated reducing the dose administered to levels which have proved clinically ineffective.

Several investigations of alternative dosage formulations for mitotane have been reported in the literature. For example, in 1961 it was reported that solutions of mitotane in corn oil were more effective in causing adrenal cortical atrophy in dogs than mitotane administered as a dry powder (Nichols, *The Adrenal Cortex*, pp. 86–89, 1961). The same year it was also reported that administration of mitotane in corn oil solution or oral Lipomul (an oil emulsion marketed by Upjohn) to subjects having adrenal carcinoma had no therapeutic advantage over mitotane administered as capsules of dry powder (Moy, *Journal of Laboratory and Clinical Medicine*, Vol. 58, No. 2, pp. 296–304, 1961). A later study on an adrenal cancer patient, however, demonstrated increased absorption of the drug upon oral administration of mitotane suspended in olive oil (Nissen-Meyer and Vogt, *Cushing's Syndrome, Diagnosis and Treatment*, pp. 141–147, William Heinemann Medical Books Ltd., 1972).

Although certain of the aforementioned prior art formulations may be an improvement over dry dosage formulations of mitotane, the prior art formulations do not maximize the absorption of mitotane sufficiently to allow the dosage to be reduced to levels where toxic side effects are substantially eliminated.

It has now been unexpectedly found that absorption of mitotane from the gastrointestinal tract can be increased significantly when the drug is administered in an oil selected from the group consisting of safflower oil, peanut oil, soybean oil, and mixtures thereof. Moreover, it has also been found that sustained levels of mitotane in the blood can be obtained when the drug is administered in one of the aforementioned oils or mixtures thereof.

Accordingly, it is an object of the present invention to provide a well tolerated, effective chemotherapeutic composition for treating adrenal cortical carcinoma in humans, which composition maximizes the absorption of mitotane sufficiently to allow the dosage of the drug to be reduced to levels where toxic side effects are substantially eliminated.

Moreover, a further object of the invention is to provide a well tolerated, effective chemotherapeutic composition for treating adrenal cortical carcinoma in humans which composition employs only 10–20% by weight of the amount of mitotane employed in dry dosage formulations.

A still further object of the invention is to provide a chemotherapeutic composition which provides sustained levels of mitotane in the blood as compared with other dosage formulations.

The above objects, features and advantages of the present invention are achieved by dissolving a pharmaceutically effective amount of mitotane in an oil carrier or vehicle selected from the group consisting of safflower oil, peanut oil, soybean oil and mixtures thereof.

Accordingly, a preferred therapeutic composition according to the present invention comprises mitotane dissolved in safflower oil. Another preferred therapeutic composition comprises mitotane dissolved in peanut oil. Still another preferred therapeutic composition comprises mitotane dissolved in soybean oil. Yet another preferred therapeutic composition comprises mitotane dissolved in a mixture of oils, said mixture containing from about 10 to 80% safflower oil, from about 20 to 90% peanut oil and from about 0 to 20% soybean oil.

The aforementioned oils should be as pure as is technically and economically feasible. Incorporation of the drug in the oil carrier is accomplished with standard techniques and practices common to the pharmaceutical field.

The ratio of mitotane to oil carrier or vehicle can vary depending on the concentration of medicament desired in the final unit dosage form. In general, however, the preparation should contain a therapeutically effective amount of mitotane, generally from about 5 to 20% by weight of the composition. The administerable pharmaceutical composition is encapsulated, preferably in unit dosage form for simple oral administration of precise dosages. The amount of mitotane administered in the formulation of the instant invention generally ranges from 100 mg. to 5 g. per day. Actual methods of preparing such dosage forms are known or will be apparent to those skilled in the art.

EXAMPLE

Formulations

A — 450 mg. mitotane in 3 ml. olive oil, via capsule.
B — 450 mg. mitotane in 3 ml. safflower oil, via capsule
C — 450 mg. mitotane in 3 ml. peanut oil, via capsule
D — 450 mg. mitotane in 3 ml. soybean oil, via capsule
E — 450 mg. mitotane powder via capsule.
F — 500 mg. mitotane via tablet.

A male beagle dog weighing 10 kg. was dosed with a single oral dose of formulation A. Blood samples were then removed at 0, ½, 1, 1½, 2, 2½, 3, 5, 8 and 12 hours posttreatment. Immediately after removal, the blood samples were allowed to clot and the serum removed. Following a four day rest period, the animal was dosed with formulation B and samples were collected as above. In like manner, samples were collected after the animal was dosed with formulations C, D, E, and F.

The collected samples were analyzed for mitotane by a modification of the procedure of Dale, et al., which is described in the *Journal of the Association of Official Analytical Chemists*, 53, pp. 1287–1292 (1970).

A. Extraction of Samples

One ml. of 23 N formic acid was added, with mixing, to 1 ml. of serum in a centrifuge tube. Thereafter, 1 ml. of analytical reagent grade hexane was added to the tube and the resulting mixture vortexed at high speed until an emulsion was formed. The emulsion was centrifuged briefly to accelerate phase separation and the hexane layer removed and transferred to a 3 ml. volumetric flask. Hexane extraction of the serum was then repeated twice and the combined extracts were then diluted to 3 ml. with additional hexane and mixed well.

B. Instrument

A Varian Model 1740 instrument equipped with a 3 ft. × ⅛ in. stainless steel column containing 1% OV-17 on Chrom. W. A/W DMCS H/P 80/100 mesh, and a 63 Ni electron capture detector was used in the detection of mitotane. The instrument was operated at a column temperature of 210° C., injector and detector temperatures of 235° C., and a nitrogen pressure and flow rate of 30 lbs. and 35 cc/min. respectively. The standing current was about $1 \times 10^{-9}$ amps.

PREPARATION OF STANDARDS AND CALIBRATION OF INSTRUMENT

Standard solutions of pure mitotane in analytical reagent grade hexane at concentrations of 0.0100, 0.100, and 1.00 ppm were prepared. One $\mu$l of each solution was injected at an attenuation of $1 \times 10^{-10}$ or $2 \times 10^{-}$ and the peak high measured. A calibration curve was established plotting nanograms of mitotane (1 mg = 1$\mu$l of 1 ppm) versus peak height.

ANALYSIS OF SAMPLES

One $\mu$l of each sample was injected at an initial attenuation of $1 \times 10^{-10}$ and the peak height of mitotane measured. The amount of mitotane in the sample was then determined from the curve and this value was then multiplied by 3 to obtain the ppm of mitotane in the original blood sample.

The following table summarizes blood levels of mitotane (ppm) observed during a 12 hour period for both dry and oil based formulations.

| BLOOD LEVELS (PPM) OF MITOTANE AFTER SINGLE ORAL DOSE IN BEAGLE DOG FORMULATIONS) | | | | | | | |
|---|---|---|---|---|---|---|---|
| Time of blood sample | Tablet 500 mg | Powder 450 mg | Olive Oil 450 mg | Corn Oil 450 mg | Soybean Oil 450 mg | Peanut Oil 450 mg | Safflower Oil 450 mg |
| 0 | ND | 0.00 | 0.00 | 0.00 | 0.00 | 0.00 | 0.00 |
| 0.5 |  | 0.02 | 0.00 | 0.08 | 0.10 | 0.00 | 0.13 |
| 1 | ND | 0.02 | 0.00 | 0.38 | 0.33 | 0.06 | 0.49 |
| 1.5 |  | 0.02 | 1.25 | 0.96 | 1.09 | 0.57 | 2.04 |
| 2 | ND | 0.02 | 1.37 | 2.20 | 1.48 | 2.16 | 3.90 |
| 2.5 |  | — | 1.66 | 1.05 |  | 2.32 | 4.77 |
| 3 |  | 0.04 | 1.42 | 0.58 | 3.40 | 3.37 | 3.77 |
| 4 | ND | 0.58 | — | — | 1.80 | 3.77 | — |
| 5 |  | — | 0.40 | 0.09 | — | — | 0.61 |
| 6 | ND | 0.05 | — | — | 0.48 | — | — |
| 8 | ND | 0.05 | 0.03 | 0.04 | 0.20 | 0.67 | 0.17 |
| 12 | ND | 0.02 | 0.00 | 0.02 | 0.10 | 0.19 | 0.10 |

ND = No mitotane could be detected in the samples taken following oral administration of the mitotane tablet.
Lower limit of detection for this method is about 0.02 ppm.

Based on the data tabulated in the foregoing table, it is readily apparent that mitotane formulated in soybean oil, peanut oil, safflower oil, or mixtures thereof is far more readily absorbed than equivalent dry dosage formulations (i.e., mitotane powder or mitotane tablet). As is evident from the data, no mitotane could be detected when a 500 mg. scored tablet was administered.

Further, it is readily apparent from the data that the absorption of mitotane formulated in soybean oil, peanut oil, safflower oil, or mixtures thereof is significantly superior to mitotane formulated in either olive oil or corn oil.

Moreover, it is readily apparent from the data that the formulations of the instant invention provide prolonged or sustained levels of the drug in the blood as opposed to dry dosage formulations or formulations employing corn oil or olive oil.

In view of the increased absorption afforded by the therapeutic compositions of the instant invention, it is possible to decrease the amount of mitotane administered and thereby eliminate many, if not all, of the undesirable side effects that have interfered with the use of the drug in the treatment of adrenal cortical carcinoma.

The invention being thus described, it will be obvious that the same may be varied in many ways. Such variations are not to be regarded as a departure from the spirit and scope of the invention, and all such modifications are intended to be within the scope of the following claims.

What is claimed is:

1. A therapeutic composition for orally treating adrenal cortical carcinoma comprising an effective amount for treating adrenal cortical carcinoma of 1,1-dichloro-2-(o-chlorophenyl)-2-(p-chlorophenyl)ethane and an oil carrier selected from the group consisting of safflower oil, peanut oil, soybean oil and mixtures thereof.

2. A therapeutic composition according to claim 1 wherein the carrier is safflower oil.

3. A therapeutic composition according to claim 1 wherein the carrier is peanut oil.

4. A therapeutic composition according to claim 1 wherein the carrier is soybean oil.

5. A therapeutic composition according to claim 1 wherein the carrier is a mixture of oils comprising from about 10 to 80% safflower oil, 20 to 90% peanut oil and 0 to 20% soybean oil.

6. A therapeutic composition according to claim 1 containing from about 5 to 15% by weight of 1,1-dichloro-2-(o-chlorophenyl)-2-(p-chlorophenyl)ethane.

7. A method for treating adrenal cortical carcinoma in humans comprising orally administering a therapeutic composition comprising an effective amount for treating adrenal cortical carcinoma of 1,1-dichloro-2-(o-chlorophenyl)-2-(p-chlorophenyl)ethane and an oil carrier selected from the group consisting of safflower oil, peanut oil, soybean oil and mixtures thereof.

8. A method according to claim 7 wherein the oil carrier is safflower oil.

9. A method according to claim 7 wherein the oil carrier is peanut oil.

10. A method according to claim 7 wherein the oil carrier is soybean oil.

11. A method according to claim 7 wherein the carrier is a mixture of oils comprising from about 10 to 80% safflower oil, 20 to 90% peanut oil and 0 to 20% soybean oil.

12. A method according to claim 7 wherein the therapeutic composition contains from about 5 to 15% by weight of 1,1-dichloro-2-(o-chlorophenyl)-2-(p-chlorophenyl)ethane.

* * * * *